US007407747B2

(12) United States Patent
Perry et al.

(10) Patent No.: US 7,407,747 B2
(45) Date of Patent: Aug. 5, 2008

(54) METHOD FOR DRYING DYE-TERMINATOR SEQUENCING REAGENTS

(75) Inventors: Kathleen M. Perry, San Francisco, CA (US); Robert E. Ruhfel, San Francisco, CA (US); Sandra L. Spurgeon, San Mateo, CA (US); Peter Ma, Cupertino, CA (US)

(73) Assignee: Applera Corporation, Foster City, CA (US)

( * ) Notice: Subject to any disclaimer, the term of this patent is extended or adjusted under 35 U.S.C. 154(b) by 483 days.

(21) Appl. No.: 10/272,450

(22) Filed: Oct. 15, 2002

(65) Prior Publication Data

US 2004/0072167 A1 Apr. 15, 2004

(51) Int. Cl.
*C12Q 1/68* (2006.01)
*C07H 21/00* (2006.01)
*C07H 21/02* (2006.01)
*C12P 19/34* (2006.01)

(52) U.S. Cl. .................. 435/6; 435/91.1; 435/91.2; 536/23.1; 536/25.3; 536/26.6

(58) Field of Classification Search ............. 435/6, 435/91.1, 91.2; 536/23.1, 25.3, 26.6
See application file for complete search history.

(56) References Cited

U.S. PATENT DOCUMENTS

| | | | | |
|---|---|---|---|---|
| 5,366,860 | A | 11/1994 | Bergot et al. | 435/6 |
| 5,800,996 | A | 9/1998 | Lee et al. | 435/6 |
| 5,844,106 | A * | 12/1998 | Seela et al. | 536/22.1 |
| 5,863,727 | A | 1/1999 | Lee et al. | 435/6 |
| 5,945,526 | A | 8/1999 | Lee et al. | 536/26.6 |
| 6,218,124 | B1 | 4/2001 | Lee | |
| 6,248,568 | B1 | 6/2001 | Khan et al. | 435/91.1 |
| 6,335,440 | B1 | 1/2002 | Lee et al. | 536/26.6 |
| 6,960,432 | B2 * | 11/2005 | Okamoto et al. | 435/6 |

FOREIGN PATENT DOCUMENTS

| | | |
|---|---|---|
| DE | 19503685 A1 | 8/1996 |
| EP | 0726310 A1 | 8/1996 |
| EP | 1247866 A1 | 10/2002 |
| WO | WO 99/10531 | 3/1999 |

OTHER PUBLICATIONS

Colaco, C., et al., "Extraordinary Stability of Enzymes Dried in Trehalose: Simplified Molecular Biology", *Biotechnology*, vol. 10, (Sep. 1992), pp. 1007-1011.
Earley, J., et al., "Efficient DNA sequencing on microtiter plates using dried reagents and Bst DNA polymerase", *J.DNA Sequencing and Mapping*, vol. 4, (1993), pp. 79-85.
Ortlepp, S., et al., "Performing Nucleic Acid Reactions Using Predispensed Lyophilized Reaction Mixtures", *BioTechniques*, vol. 7, No. 10, (1989), pp. 1110-1111, 1113-1115.
Sanger, F., et al., "DNA sequencing with chain-terminating inhibitors", *Proc. Natl. Acad. Sci. USA*, vol. 74, No. 12, (Dec. 1977), pp. 5463-5467.
Uritani, M., et al., "Protective Effect of Disaccharides on Restriction Endonucleases during Drying under Vacuum", *J. Biochem.*, vol. 117, No. 4, (Apr. 1995), pp. 774-779.
PCT Search Report for International Application No. PCT/US03/33093, (May 15, 2004),2 pages.
Y.Yan et al., "Identification of Nucleotides with Identical Fluorescent Labels Based on Fluorescence Polarization in Surfactant Solutions" Analytical Chemistry, vol. 73, No. 18, Sep. 15, 2001, pp. 4508-4513.
Supplementary European Search Report issued on May 10, 2006 in co-pending European Patent Application No. 03773287.2, 4 pages.

* cited by examiner

*Primary Examiner*—Jezia Riley
(74) *Attorney, Agent, or Firm*—Andrew K. Finn

(57) ABSTRACT

A dry composition comprising a nucleotide linked to a fluorescent dye is provided. A method of making a dry composition comprising the step of drying a solution comprising a nucleotide linked to a fluorescent dye is provided. A method is provided for performing a reaction on a nucleic acid substrate comprising: (a) providing a vessel containing a dried composition comprising a nucleotide linked to a fluorescent dye, and (b) adding to the vessel an aqueous solution and the nucleic acid substrate. A kit is provided for determining the sequence of a nucleic acid, the kit comprising a dry composition comprising a nucleotide linked to a fluorescent dye.

15 Claims, No Drawings

SEQUENCE LISTING

<160> NUMBER OF SEQ ID NOS: 1

<210> SEQ ID NO 1
<211> LENGTH: 18
<212> TYPE: DNA

```
<213> ORGANISM: Artificial Sequence
<220> FEATURE:
<223> OTHER INFORMATION: A primer

<400> SEQUENCE: 1
tgtaaaacga cggccagt                                                 18
```

METHOD FOR DRYING DYE-TERMINATOR SEQUENCING REAGENTS

BACKGROUND

DNA sequencing is of increasing importance in biological research, biotechnology, medical diagnostics, forensics, and other fields. Most sequencing is done by the dideoxy chain termination method (Sanger et al., 1977; Slatko et al., 1991). Sequencing reactions generally involve the dispensing of several liquid aliquots: a DNA polymerase, four deoxynucleotides, four chain terminators, and sometimes buffer or other components.

Sequencing today generally uses fluorescently labeled dideoxynucleotide terminators. The four fluorescently labeled dideoxynucleotides can be used in a single reaction mixture, and spectrally resolved with electrophoresis in a single lane. See Bergot et al., U.S. Pat. No. 5,366,860. The fluorescent labels constitute a greater chemical alteration of the nucleotides than do the radioactive labels. The fluorescent labels are complex groups that potentially can be damaged during drying. Recently, improved fluorescent labels have been introduced that are energy transfer dyes. See Lee et al., U.S. Pat. Nos. 5,800,996; 5,863,727; 5,945,526; and 6,335,440. In energy transfer dyes, a donor dye absorbs incoming radiation and transfers the excitation energy to an acceptor dye that is linked to the donor dye. The acceptor dye then emits radiation at a wavelength of lower energy than the wavelength of peak absorption for the donor dye. Energy transfer dyes offer improved fluorescence yield and better spectral resolution of the four dyes needed in a sequencing reaction. However, they are larger and more complicated molecules than standard dyes, and thus could be more sensitive to damage by desiccation or other environmental stress.

There is a need for methods of DNA sequencing, and other methods of nucleic acid analysis involving nucleic acid labeling, that use dried fluorescent reagents. There is also a need for methods in which the polymerase and all reagents, including four labeled chain terminators, are dried in a single well to eliminate the need to transfer solutions between wells.

SUMMARY OF THE INVENTION

One embodiment of the present invention provides a dry composition containing a nucleotide linked to a fluorescent dye.

Another embodiment of the present invention provides a method of making a dry composition containing a nucleotide linked to a fluorescent dye, the method involving the step of drying a solution containing the nucleotide linked to a fluorescent dye.

Another embodiment of the present invention provides a method of performing a reaction on a nucleic acid substrate involving: (a) providing a vessel containing a dried composition containing a nucleotide linked to a fluorescent dye, and (b) adding to the vessel an aqueous fluid and the nucleic acid substrate.

Another embodiment of the present invention provides a kit for determining the sequence of a nucleic acid, the kit having a dry composition containing a nucleotide linked to a fluorescent dye.

DETAILED DESCRIPTION

Definitions

"Nucleotide" as used herein includes both deoxyribonucleotides and ribonucleotides, as well as modified nucleotides such as dideoxynucleotides and other chain terminator nucleotides. It also includes nucleotide residues within a polynucleotide.

"Fluorescent dye" as used herein refers to a dye whose presence can be detected by fluorescence. In particular embodiments, the fluorescent dyes used herein are suitable for nucleic acid sequencing. For instance, in a composition containing four chain terminator nucleotides, each linked to a different fluorescent dye, each of the four fluorescent dyes will emit at a peak emission wavelength that is spectrally resolvable from the peak emission wavelengths of the other dyes. The dyes also may absorb at a wavelength that does not interfere with monitoring emission from any of the dyes.

"Solution" refers to a composition containing a solvent in which the nucleotide linked to a fluorescent dye is at least partly dissolved, and/or in which another specified component of the composition, is at least partly dissolved. Solutions can also contain other components that are suspended, settled, or otherwise not dissolved. An example of a solution is an aqueous solution.

"Solvents" refers to substances in which components of the dry composition can be dissolved. Solvents can be substantially removed in the process of making the dry composition by sublimation, evaporation, boiling, or extraction by other solvents. An example of a solvent is water.

"Dry composition" refers to a composition that is substantially free of solvent. In particular embodiments, the dry compositions of the invention can have less than 25%, less than 20%, less than 15%, less than 10%, less than 7%, less than 5%, less than 3%, less than 2%, or less than 1% total solvent content by weight. Residual solvent present in the dry composition can be complexed to the nucleotide linked to a fluorescent dye, or can be complexed to carbohydrate, protein, salt, or other component of the dry composition.

"Aqueous solution" as used herein refers to a composition containing any amount of water, in either a liquid or solid form. An aqueous composition may also contain one or more other solvents that are miscible or immiscible with water, and those solvents may be present in greater or lesser amounts in the aqueous composition than the water.

"Drying" as used herein refers to the removal of water or other solvents by any means, including sublimation, evaporation, boiling, and solvent extraction.

The term "nucleic acid polymerase" includes DNA polymerases and RNA polymerases. The DNA polymerases can be DNA-dependent or RNA-dependent (i.e., reverse transcriptase).

The term "thermostable nucleic acid polymerase" refers to a DNA polymerase that retains at least 90% of its activity after incubation in an appropriate buffer at 50° C. for 10 minutes. In certain embodiments, a thermostable nucleic acid polymerase retains at least 90% of its activity after incubation in an appropriate buffer for 10 minutes at 55° C., 60° C., 65° C., 70° C., 80° C., or 90° C.

The term "Taq DNA polymerase" (Thermus aquaticus DNA polymerase) includes mutant forms of Taq DNA polymerase, such as Taq G46D F667Y DNA polymerase.

The term "nucleic acid substrate" as used herein refers to a nucleic acid that is modified by a chemical or enzymatic reaction, or to a nucleic acid that serves as a template for a chemical or enzymatic reaction. For instance, in a nucleic acid sequencing reaction, both the oligonucleotide that is extended by a polymerase and the template nucleic acid are "nucleic acid substrates," as the term is used herein.

As used herein, the term "chain terminator nucleotide" refers to a mononucleotide that can be incorporated into a growing polynucleotide chain by a nucleic acid polymerase and that when incorporated terminates the chain because a polynucleotide containing the chain terminator nucleotide at its 3' terminus cannot serve as a substrate for the addition of another nucleotide by the nucleic acid polymerase. Typical terminators are those in which the nucleobase is a purine, a 7-deaza-purine, a pyrimidine, a normal nucleobase or a common analog thereof and the sugar moiety is a pentose which includes a 3'-substituent that blocks further synthesis, such as a ddNTP. Substituents that block further synthesis include, but are not limited to, amino, deoxy, halogen, alkoxy and aryloxy groups. Exemplary terminators include, but are not limited to, those in which the sugar-phosphate ester moiety is 3'-($C_1$-$C_6$) alkylribose-5'-triphosphate, 2'-deoxy-3'-($C_1$-$C_6$) alkylribose-5'-triphosphate, 2'-deoxy-3'-($C_1$-$C_6$)alkoxyribose-5'-triphosphate, 2'-deoxy-3'-($C_5$-$C_{14}$)aryloxyribose-5'-triphosphate, 2'-deoxy-3'-haloribose-5'-triphosphate, 2'-deoxy-3'-aminoribose-5'-triphosphate, 2',3'-dideoxyribose-5'-triphosphate or 2',3'-didehydroribose-5'-triphosphate.

The term "energy transfer dye" as used herein refers to a dye containing two fluorophores connected to each other by a linker. Ordinarily, the linker will form a covalent linkage. The donor fluorophore absorbs excitation energy and emits at a wavelength that is absorbed by the acceptor fluorophore. After absorbing this photon, the acceptor fluorophore in turn emits at a longer wavelength. Examples of energy transfer dyes can be found in U.S. Pat. Nos. 5,863,727; 5,800,996; 5,945,526; and 6,335,440.

The term "cryoprotectant" refers to a substance that, when included in aqueous solutions, protects enzymes dissolved in the aqueous solutions from loss of enzymatic activity due to drying or freezing of the aqueous solutions. Examples of cryoprotectants include carbohydrates and polyols, such as trehalose, glucose, sucrose, glycerol, polyethylene glycol, and sorbitol.

The terms "unsaturated five-membered ring," "unsaturated six-membered ring," and "fused ring system" include ring systems where the ring atoms are all carbon and ring systems where some ring atoms are heteroatoms. The rings may be aromatic or non-aromatic. The terms "unsaturated five-membered ring" and "unsaturated six-membered ring" refer to moieties with one or more unsaturated bond in the ring.

As used herein, "xanthene dyes," "asymmetric benzoxanthene dyes," "rhodamine dyes," "fluorescein dyes," "4,7-dichlororhodamine dyes," "4,7-dichlorofluorescein dyes," "carboxyfluorescein dyes," "carboxyrhodamine dyes," "carboxy R110 dyes," "carboxy R6G dyes," "carboxy-X-rhodamine dyes," "cyanine dyes," "phthalocyanine dyes," "squaraine dyes," and "Cy5" are as defined or used in U.S. Pat. No. 6,335,440, which is hereby incorporated by reference.

As used herein, the term "unconcentrated nucleic acid derived from lysed whole cells" refers to nucleic acid derived from lysed whole cells that is not concentrated after the cells are lysed. The term "unconcentrated nucleic acid" also includes nucleic acid that is diluted after lysis of the whole cells.

Description

The present invention concerns a dry composition comprising a nucleotide linked to a fluorescent dye. The dry compositions of the invention can be used in reactions on nucleic acid substrates, such as nucleic acid sequencing reactions. An advantage of using some embodiments of the dry compositions of the invention in sequencing reactions is that the dry compositions allow the use of a large volume of template, and therefore the use of more dilute template samples. This embodiment, for instance, facilitates the sequencing of templates directly from lysed whole cells. The whole cells can be derived from colonies or suspensions of cells. With the dry compositions of the invention, in some embodiments the template can more easily be sequenced without concentration from the suspension of lysed whole cells.

Another advantage of using some embodiments of the dry compositions of the invention, is that all the components required for a sequencing reaction can be dried in a single vessel. This aspect of certain embodiments of the invention saves time and prevents possible error by an experimenter in dispensing multiple components into a sequencing reaction mixture.

In certain embodiments of the dry compositions of the invention, four different fluorescent dyes will be linked to chain terminator nucleotides, e.g., the four different 2',3'-dideoxynucleotides, for use in a chain termination sequencing reaction that may be analyzed by an automated fluorescence detecting nucleic fragment analyzer (e.g. ABI 3100). The fluorescent sequencing reaction may involve thermal cycling using a thermostable polymerase, such as Taq DNA polymerase. In certain embodiments, all the components, except template and optionally the sequencing primer, needed for a sequencing reaction—such as the four nucleoside triphosphates, the nucleic acid polymerase, buffers and salts, and optionally the sequencing primer—will be dried together with the four dideoxynucleotides linked to four different fluorescent dyes to form a single dried composition in a vessel, such as the well of a multiwell plate. In certain embodiments, the composition will also include a cryoprotectant such as trehalose. The template DNA in water or aqueous solution, and optionally the sequencing primer, then can be added to the well to resuspend the components, and the suspension or solution formed can be used directly in a sequencing reaction. In another example, water (or an aqueous solution containing other components needed for the sequencing reaction) may be used to resuspend the dried components, and the template DNA added subsequently.

The dry compositions of the invention exhibit unexpected stability. In particular embodiments, a dry composition containing a nucleotide linked to a fluorescent dye, after storage at 23° C. for 8 weeks (capped, desiccated, and protected from light), when used in a nucleic acid sequencing reaction, such as that described in Example 3, generates extended polynucleotide products with at least 50%, at least 60%, at least 70%, at least 80%, or at least 90% as much fluorescent signal strength as the corresponding dry composition immediately after drying or after storage for 1 week at 23° C., or the corresponding aqueous composition that was never dried.

In one embodiment of a dry composition comprising a nucleotide linked to a fluorescent dye, the nucleotide is part of a polynucleotide. In another embodiment, the nucleotide is a mononucleotide. In some embodiments, the mononucleotide may include a chain terminator nucleotide.

In one embodiment, the nucleotide is a chain terminator nucleotide. In a specific embodiment of the composition involving a chain terminator nucleotide, the composition also has three other chain terminator nucleotides, each linked to a fluorescent dye, wherein each of the chain terminator nucleotides is linked to a different fluorescent dye. In particular embodiments, the chain terminator nucleotides are 2',3'-dideoxynucleotides. In one embodiment of the composition with four chain terminator nucleotides linked to four fluorescent dyes, the composition further contains four nucleoside triphosphates.

In another embodiment, the composition further contains a nucleic acid polymerase. In one embodiment, the nucleic acid polymerase is a thermostable nucleic acid polymerase. In one embodiment where the polymerase is thermostable, the polymerase is Taq DNA polymerase. In a particular embodiment where the polymerase is Taq DNA polymerase, the polymerase is Taq G46D F667Y DNA polymerase. In one embodiment, the composition contains Taq DNA polymerase and another nucleic acid polymerase.

In one embodiment, the composition contains a cryoprotectant. In specific embodiments, the cryoprotectant is trehalose or sucrose.

In one embodiment, the composition is substantially free of glycerol. In a specific embodiment, the composition contains no glycerol. In a specific embodiment where the composition is substantially free of glycerol, the composition contains a thermostable nucleic acid polymerase, and the ratio of glycerol to thermostable nucleic acid polymerase is less than 20, less than 10, less than 5, less than 3, less than 1, less than 0.5, or less than 0.1 μg glycerol per unit of thermostable nucleic acid polymerase. As used herein, a unit of nucleic acid polymerase is defined as the quantity of enzyme that incorporates 10 nmoles of nucleotides into acid insoluble material in 30 minutes at the optimal temperature and buffer conditions for the enzyme. For instance, a unit of Taq DNA polymerase is the quantity of enzyme that incorporates 10 nmoles of deoxynucleotides into acid insoluble material in 30 minutes at 75° C. in 20 mM Tris-HCl, 10 mM KCl, 2 mM $MgCT_2$, 0.1% TRITON X-100, 10 mM ammonium sulfate, 200 μM each dNTP, and 200 μg/ml activated calf thymus DNA, pH 8.8 (pH measured at 25° C.).

The inventors surprisingly found that dry compositions substantially free of glycerol were more stable for storage, gave stronger signals in nucleic acid sequencing reactions, and gave better sequencing quality in nucleic acid sequencing reactions than comparable compositions containing glycerol. Without wishing to be bound by theory, the inventors hypothesize that glycerol absorbs moisture from the atmosphere, and that this destabilizes components of the dry compositions, most likely the nucleotide, dye, or the linker between the nucleotide and dye, or the nucleic acid polymerase. The absorbed moisture, for instance, could lead to very high concentrations of dissolved salt or buffer in the moisture. High salt concentrations can destabilize enzymes. Buffers, such as Tris, often give very different pHs at high concentrations than they do at lower concentrations. Thus, absorbed moisture could cause the composition to have an extreme pH that destabilizes components of the composition. In addition, absorbed moisture itself could destablize components of the composition. It may promote enzyme denaturation and hydrolysis or other chemical modification of the nucleotides, dyes, or linkers. It should be noted that most enzymes are stored in glycerol, and glycerol can be removed by dialysis, filtration, size exclusion chromatography, or other means.

In one embodiment of the composition, the fluorescent dye linked to a nucleotide is an energy transfer dye containing a donor connected to an acceptor by a linker. In specific embodiments, the linker contains an alkene, diene, alkyne, unsaturated five-membered ring, unsaturated six-membered ring, or a fused ring system. Particular examples of five- or six-membered rings which may be used include, but are not limited to, cyclopentene, cyclohexene, cyclopentadiene, cyclohexadiene, furan, thiofuran, pyrrole, isopyrrole, isoazole, pyrazole, isoimidazole, pyran, pyrone, benzene, pyridine, pyridazine, pyrimidine, pyrazine, and oxazine. Examples of fused ring structures include, but are not limited to, indene, benzofuran, thionaphthene, indole, and naphthalene.

In one embodiment of the composition, the fluorescent dye is an energy transfer dye having the structure

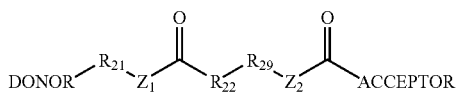

where $R_{21}$ is a $C_{1-5}$ alkyl;

$Z_1$ is NH, sulfur, or oxygen;

$R_{22}$ is an alkene, diene, alkyne, unsaturated five-membered ring, unsaturated six-membered ring, or a fused ring system;

$R_{29}$ is $C_1$-$C_5$ alkyl; and $Z_2$ is NH, sulfur, or oxygen.

In one embodiment of the composition where the dye is an energy transfer dye containing a donor connected to an acceptor by a linker, the donor is a fluorescein, rhodamine, or asymmetric benzoxanthene dye.

In specific embodiments, the donor is a carboxyfluorescein; 4,7-dichlorofluorescein; asymmetric benzoxanthene; rhodamine; 4,7-dichlororhodamine; carboxyrhodamine; carboxy R110; carboxy R6G; or carboxy-X-rhodamine dye; or is Cy5.

In specific embodiments, the acceptor is a xanthene, cyanine, phthalocyanine, or squaraine dye. In specific embodiments where the acceptor is a xanthene, cyanine, phthalocyanine, or squaraine dye, the acceptor is a carboxyfluorescein; 4,7-dichlorofluorescein; asymmetric benzoxanthene; rhodamine; 4,7-dichlororhodamine; carboxyrhodamine; carboxy R110; carboxy R6G; or carboxy-X-rhodamine dye; or is Cy5.

Another embodiment of the invention is a method of making a dry composition containing a nucleotide linked to a fluorescent dye, the method involving the step of drying a solution containing a nucleotide linked to a fluorescent dye. If the dry composition contains other components besides the nucleotide linked to a fluorescent dye, then in the method of making the dry composition the other components of the dry composition can also be dried from one or more solutions. The solution containing the nucleotide linked to the fluorescent dye can be the same as one or more of the one or more solutions containing the other components of the dry composition. For instance, all the components can be in one solution that is dried, different components can be in different solutions that are dried sequentially in one vessel, or different components can be in different solutions that are dried separately in different vessels and then the dry components mixed.

In a particular embodiment of the method of making a dry composition, the nucleotide linked to a fluorescent dye is a chain terminator nucleotide. In a particular embodiment where the nucleotide is a chain terminator nucleotide, the method further involves drying one or more solutions collectively containing three other chain terminator nucleotides, each of the four chain terminator nucleotides being linked to a fluorescent dye, wherein each of the four chain terminator nucleotides is linked to a different fluorescent dye.

In a particular embodiment of the method of making a dry composition, the method further involves drying one or more solutions collectively comprising four nucleoside triphosphates.

In a particular embodiment of the method of making a dry composition, the method further involves drying a solution containing a nucleic acid polymerase. In a particular embodiment, the nucleic acid polymerase is a thermostable nucleic acid polymerase. In a specific embodiment where the polymerase is thermostable, the polymerase is Taq DNA polymerase.

In a particular embodiment of the method of making a dry composition involving drying a solution containing a thermostable nucleic acid polymerase, the solution containing the nucleic acid polymerase is substantially free of glycerol. Optionally, the solution containing the nucleotide linked to a fluorescent dye, if it is a separate solution, is also substantially free of glycerol. In particular embodiments, the starting solutions that are substantially free of glycerol prior to drying contain on a weight to volume basis less than 2, less than 1, less than 0.7, less than 0.3, less than 0.2, less than less than 0.1, or less than 0.05 percent glycerol, or contain no glycerol.

In a particular embodiment of the method of making a dry composition involving drying a solution containing a thermostable nucleic acid polymerase, the solution containing the thermostable nucleic acid polymerase contains a cryoprotectant. In particular embodiments, the cryoprotectant is trehalose or sucrose.

In a particular embodiment of the method of making a dry composition, the aqueous composition further contains a cryoprotectant. In particular embodiments, the cryoprotectant is trehalose or sucrose.

In a particular embodiment of the method of making a dry composition, the temperature of the solution during at least a portion of the drying step is less than 0° C. In a particular embodiment of the method of making a dry composition involving drying a solution containing a thermostable nucleic acid polymerase, the solution containing the thermostable nucleic acid polymerase during at least a portion of the drying step is less than 0° C.

Another embodiment of the invention provides a method of performing a reaction on a nucleic acid substrate, the method involving: (a) providing a vessel containing a dried composition comprising a nucleotide linked to a fluorescent dye, and (b) adding to the vessel an aqueous fluid and the nucleic acid substrate.

In a specific embodiment of the method of performing the reaction, the reaction is a nucleic acid sequencing reaction, and the method further comprises extending a primer hybridized to the nucleic acid substrate with a thermostable nucleic acid polymerase and determining the nucleotide sequence of at least a portion of the nucleic acid substrate. The reaction thereby forms extended nucleic acid products containing the fluorescent dye. In particular embodiments, after storage of the dry composition containing a nucleotide linked to a fluorescent dye and a thermostable nucleic acid polymerase at 23° C. for 8 weeks (capped, desiccated, and protected from light), the reaction produces a quantity of extended nucleic acid products containing at least 50%, at least 60%, at least 70, or at least 80% as much of the fluorescent dye as an identical reaction performed with the dry composition immediately after drying or 1 week after drying, with storage of the dry composition during the 1 week at 23° C., or as an identical reaction performed with the corresponding aqueous composition that was never dried.

In a specific embodiment of the method of performing a reaction on a nucleic acid substrate, the nucleic acid substrate is unconcentrated nucleic acid derived from lysed whole cells. In particular embodiments, the cells are bacterial, animal, fungal, or plant cells. The unconcentrated nucleic acid may be partially purified from the extract of the lysed whole cells. For instance, after cell lysis, debris may be centrifuged out. Undesired components may also be removed, such as by precipitation or by binding to a solid substrate.

In another embodiment, the nucleic acid substrate used in the method of performing a reaction on a nucleic acid substrate is derived from lysed whole cells and is concentrated by a factor of no more than 3 relative to its concentration in an extracellular extract immediately after lysis of the cells. For instance, the nucleic acid substrate may be partially purified by binding to solid support and then eluted from the solid support and used in a reaction.

Another embodiment of the invention provides a kit for determining the sequence of a nucleic acid, the kit containing one of the dry compositions described herein having a nucleotide linked to a fluorescent dye.

In a specific embodiment, the kit contains three or more substantially identical dry compositions containing the nucleotide linked to a fluorescent dye, the dry compositions arranged in a regular pattern on a solid substrate.

Optionally, the dry compositions of the invention may be stored sealed so as to minimize air exchange, desiccated, and protected from light. The seal need not necessarily be absolutely gas-tight. It may be sufficient to minimize gas exchange. The compositions may also be stored under an inert gas, such as argon or nitrogen.

The process of drying a solution containing a nucleotide linked to a fluorescent dye can be done by any process and at any temperature which maintains the stability of the fluorescent dye, the nucleotide, and their linkage. Likewise, the process of drying a solution containing a nucleic acid polymerase and a solution containing any other component of the invention can be done by any process and at any temperature that maintains the stability of the polymerase or the other components. By "maintaining stability" it is meant that after drying, the nucleotide linked to a fluorescent dye, the polymerase, and any other specified component, is still suitable for use in a nucleic acid sequencing reaction or in another intended use of the dry composition. The solutions can be dried under vacuum, by air drying, or under atmospheric pressure under another gas, such as an inert gas (e.g., nitrogen or argon). In particular embodiments, the solutions are dried at room temperature, with mild heating, or at a reduced temperature. In a particular embodiment, the solutions are frozen and then dried under vacuum (i.e., lyophilized). The process of drying is continued until the compositions are substantially free of solvent. In particular embodiments, the dry compositions resulting from the drying process can have less than 25%, less than 20%, less than 15%, less than 10%, less than 7%, less than 5%, less than 3%, less than 2%, or less than 1% total solvent content by weight.

EXAMPLES

The DNA polymerase used in the following examples was Taq G46D F667Y DNA polymerase, commercially available as AMPLITAQ DNA polymerase FS (Applied Biosystems, Foster City, Calif.).

Example 1

Freeze-Drying Taq G46D F667Y DNA Polymerase with and without Template DNA

Ten µl of a 10 µM solution of Taq G46D F667Y DNA polymerase in storage buffer (50% w/v glycerol, 100 mM KCl, 20 mM Tris-HCl, pH 8.0, 0.1 mM EDTA, 1 mM dithiothreitol, 0.5% TWEEN 20, 0.5% TRITON X-100) was mixed with 6 µl of 1× buffer (80 mM Tris-HCl, pH 9.0, 2.4 mM $MgCl_2$) and 4 µl of 1 mM FAS14 (+DNA sample and control) or water (−DNA sample). FAS14 is the template DNA. It forms a hairpin loop, allowing extension of the hairpin loop by the polymerase.

Control samples were kept on ice. Experimental +DNA and −DNA samples were frozen in liquid nitrogen and then dried in a SPEEDVAC (Savant Model SVC 100 H) without added heat.

The control samples and dried samples were each reconstituted with 2 ml of 1× buffer and incubated at 60° C. for 10 minutes. Four µl of FAS14 was added to the −DNA samples. The reactions were initiated by addition of 8 µl of a solution of 25 mM of each of the four dNTPs. After 5 minutes, reactions were quenched with addition of 50 µl of 60 mM EDTA. The samples were then analyzed for the presence of extended product. The results are shown below.

TABLE 1

Taq G46D F667Y DNA polymerase activity after freeze-drying.

| Sample | Concentration of extended DNA product (Arbitrary Units) |
| --- | --- |
| Control | 518 ± 6 (n = 2) |
| +DNA | 596 ± 21 (n = 3) |
| −DNA | 564 ± 10 (n = 3) |

The results show that freeze-dried Taq G46D F667Y DNA polymerase retained all of its activity. It made no significant difference whether the enzyme was frozen with template DNA or without.

Example 2

Effect on Energy-Transfer Fluorescent Dye Terminator DNA Sequencing Kit of Freeze-Drying and Storage Sequencing samples of BIGDYE TERMINATOR READY REACTION MIX version 1.0 (BDT kit) and BIGDYE TERMINATOR READY REACTION MIX v1.0 with TMANO added were frozen and dried in 10 µl aliquots.

Sequencing samples were prepared with 4 µl of TAQFS/dNTP/ddNTP BIGDYE READY REACTION MIX premix, to which was added water, primer, and optionally trimethylamine-N-oxide (TMANO), to a final volume of 10 µl. The primer was 21M13 primer (5'-TGTAAAACGACGGCCAGT-3'; SEQ ID NO:1). When present, TMANO was at a final concentration of 2 M. TMANO is reported to help renature denatured proteins. BIGDYE TERMINATOR READY REACTION MIX v1.0 contains Taq G46D F667Y DNA polymerase, a heat-stable pyrophophatase, four dNTPs, and four dideoxyterminator nucleotides labeled with fluorescein donor dyes linked to rhodamine acceptor dyes. The acceptor dyes are dichloroR6G for A, dichloroROX for C, dichloroTAMRA for T, and dichloroR110 for G.

Sequencing samples containing the BIGDYE READY REACTION MIX premix and primer and optionally TMANO were frozen in 10 µl aliquots on dry ice and then evaporated to dryness in a SPEEDVAC with no added heat for 3 hours.

After one day or 45 days of storage at room temperature, in capped (not airtight) vials, desiccated and protected from light, the dried mixes were reconstituted with 10 µl water containing 400 ng pGEM (Promega, Madison, Wis.) template DNA. Control reaction mixtures were used as is, without freezing or drying, in sequencing reactions. Sequencing reactions were performed in an Applied Biosystems Thermal Cycler 9600 or 9700. Twenty-five cycles of 95° C./10 seconds, 50° C./5 seconds, and 60° C./4 minutes were performed.

Samples were loaded on an ABI PRISM 377 DNA Sequencer (Applied Biosystems, Foster City, Calif.). Signal was collected by DYESET E and analyzed by Sequencing Analysis software. The results are shown below in Table 2.

The sequencing mixtures without TMANO retained almost complete activity after freezing and drying on the SPEEDVAC. There was slightly more loss of activity with freezing and drying when TMANO was included in the mixtures. However, whether with or without TMANO, the dried sequencing mixtures lost approximately half their activity after storage for 45 days.

TABLE 2

Effect on fluorescence signal intensity of freeze-drying and storage at room temperature of fluorescence sequencing kits.

| Sample | Fluorescence Intensity (Arbitrary Units) | | | |
|---|---|---|---|---|
| | G | A | T | C |
| BDT kit (control) | 786 | 897 | 670 | 720 |
| BDT kit (1 day after freeze-drying) | 766 | 830 | 638 | 813 |
| BDT kit (45 days after freeze-drying) | 136 | 502 | 382 | 389 |
| BDT kit + TMANO (control) | 648 | 1027 | 1101 | 1237 |
| BDT kit + TMANO (1 day after freeze-drying) | 594 | 940 | 946 | 1220 |
| BDT kit + TMANO (45 days after freeze-drying) | 229 | 660 | 519 | 682 |

Example 3

Comparison of Drying Conditions

Drying of samples was tested with various cryoprotectants and various drying conditions to identify conditions that allow the best retention of signal amplitude and signal quality in DNA sequencing.

In this Example, BIGDYE READY REACTION MIX v3.0 (Applied Biosystems, Foster City, Calif.) was used.

Sequencing samples were prepared with 2 µl TAQFS/dNTP/ddNTP BIGDYE READY REACTION MIX v3.0 premix, which contains 3 units Taq G46D F667Y DNA polymerase, a heat stable pyrophosphatase, four dNTPs, and the four BIGDYE dideoxyterminators, which are ddATP, ddCTP, ddGTP, and ddTTP, each labeled with a different energy transfer fluorescent dye. The dideoxyterminators used in BIGDYE READY REACTION MIX v3.0 are coupled to energy transfer fluorescent dyes that are different from the dyes used in v1.0, which was used in Example 2.

To 2 µl of BIGDYE READY REACTION MIX v3.0 premix was added water, and optionally primer, optionally trehalose, sucrose, or glucose, and optionally trimethylamine-N-oxide (TMANO), to a final volume of 5 µl. The primer was 21M13 primer (5'-TGTAAAACGACGGCCAGT-3'; SEQ ID NO:1). 3.2 pmol primer was used. When present, trehalose, glucose, or sucrose were at 200 mM final concentration. When present, TMANO was at a final concentration of 500 mM.

The 5 µl sequencing samples were dried in three ways: (1) Freeze-dried (frozen on dry ice and then dried at low temperature in a lyophilizer). (2) SPEEDVAC drying without heat. (Samples were frozen on dry ice, then dried in the SPEEDVAC with no added heat. In this treatment the samples went from ice to liquid during the drying.) (3) SPEEDVAC drying with medium heat. (Samples were frozen on dry ice, then dried in the SPEEDVAC at a medium heat setting.) (4) Air drying at room temperature. (Samples were not frozen before air drying.) After drying, the samples were reconstituted with 5 µl water containing 200 ng pGEM (Promega, Madison, Wis.) template DNA.

Sequencing reactions were performed in an Applied Biosystems Thermal Cycler 9600 or 9700 with twenty-five cycles of 95° C./10 seconds, 50° C./5 seconds, and 60° C./4 minutes.

Samples were loaded on an ABI PRISM 377 DNA Sequencer (Applied Biosystems, Foster City, Calif.). The same volume of sample was loaded on the sequencer in all cases. Signal was collected by DYESET E and analyzed by Sequencing Analysis software. Signal quality was measured as a Phred20 score, which is the number of bases with a Phred score of greater than 20.

The results are shown below in Tables 3-6. In Table 4, the sequencing mixes were 2 µl total volume (reagents were at the same concentrations) before drying and were reconstituted to 2 µl for the sequencing reactions.

TABLE 3

| | SPEEDVAC w/primer | | Air dry w/primer | |
|---|---|---|---|---|
| | Total Signal | Phred 20 | Total Signal | Phred 20 |
| water | 2220 | 468 | 3057 | 509 |
| trehalose | 2376 | 492 | 2989 | 524 |
| sucrose | 2724 | 497 | 1720 | 509 |
| glucose | 2598 | 506 | 193 | 306 |

TABLE 4

2 μl Formulation, SPEEDVAC w/medium heat

| | w/primer, w/TMANO | | w/primer, w/o TMANO | | w/o primer, w/TMANO | | w/o primer, w/o TMANO | |
|---|---|---|---|---|---|---|---|---|
| | Total Signal | Phred 20 | Total Signal | Phred 20 | Total Signal | Phred 20 | Total Signal | Phred 20 |
| water | 50 | 15 | 666 | 397 | 62 | 11 | 684 | 415 |
| trehalose | 1004 | 519 | 486 | 482 | 737 | 491 | 587 | 498 |
| sucrose | 636 | 499 | 825 | 497 | 863 | 488 | 684 | 467 |
| glucose | 593 | 463 | 684 | 476 | 381 | 400 | 758 | 500 |

TABLE 5

5 μl Formulation, SPEEDVAC w/medium heat

| | w/primer, w/TMANO | | w/primer, w/o TMANO | | w/o primer, w/TMANO | | w/o primer, w/o TMANO | |
|---|---|---|---|---|---|---|---|---|
| | Total Signal | Phred 20 | Total Signal | Phred 20 | Total Signal | Phred 20 | Total Signal | Phred 20 |
| water | 159 | 292 | 902 | 395 | 159 | 263 | 819 | 420 |
| trehalose | 733 | 451 | 831 | 450 | 1035 | 438 | 926 | 480 |
| sucrose | 1095 | 506 | 1017 | 480 | 1002 | 455 | 1000 | 511 |
| glucose | 1374 | 382 | 836 | 468 | 1383 | 379 | 997 | 516 |

TABLE 6

5 μl Formulation

| | Freeze-dry | | | | SPEEDVAC w/medium heat | | | |
|---|---|---|---|---|---|---|---|---|
| | w/primer, w/TMANO | | w/primer, w/o TMANO | | w/o primer, w/TMANO | | w/o primer, w/o TMANO | |
| | Total Signal | Phred 20 | Total Signal | Phred 20 | Total Signal | Phred 20 | Total Signal | Phred 20 |
| water | 218 | 428 | 70 | 133 | 119 | 378 | 49 | 130 |
| trehalose | 1337 | 580 | 1032 | 585 | 793 | 626 | 52 | 165 |

The data of Table 3 indicate that there was little difference in sequencing amplitude or quality for samples dried without added cryoprotectant or with trehalose between air drying and drying with a SPEEDVAC at room temperature. Samples with sucrose and glucose added performed better with SPEEDVAC drying than with air drying.

Tables 4 and 5 show that reaction mixes dried at medium heat setting with a SPEEDVAC with TMANO gave poor sequencing results unless a cryoprotectant was added to the mix. Trehalose and sucrose gave better protection than glucose. Glucose also had some effectiveness as a cryoprotectant.

Comparing the results of Table 3 with those of Tables 4 and 5 indicates that drying at lower temperatures was more effective than drying at medium heat with a SPEEDVAC. In Table 6, freeze-drying is compared with drying samples with a SPEEDVAC at medium heat for 3 hours, for samples without an added cryoprotectant, and those with trehalose. Freeze-drying appeared generally to be superior. The samples with trehalose gave superior results to those without trehalose.

The sequencing samples contained 2.8% (w/v) glycerol final concentration, as a result of glycerol present in the Taq G46D F667Y DNA polymerase. However, the results in Tables 4, 5 and 6 without added cryoprotectant indicate that glycerol at the concentrations used was not particularly effective as a cryoprotectant. It was noted that all these samples with glycerol never appeared to become completely dry. After drying, the samples were in the form of a shiny film, instead of a dry powder. To test the effect of eliminating glycerol, the Taq G46D F667Y DNA polymerase was buffer exchanged through an ULTRAFREE-15 centrifugal filter with drying buffer. The drying buffer was 20 mM Tris-HCl, pH 8.0, 100 mM KCl, 1 mM DTT, 0.1 mM EDTA, 0.2% (w/v) TWEEN 20, 100 mM trehalose. After buffer exchange to remove the glycerol, the Taq G46D F667Y DNA polymerase was added to the other components to prepare TAQFS/dNTP/ddNTP BIGDYE READY REACTION MIX v3.0 premix lacking glycerol, which was used in drying experiments as described above for premix containing glycerol. The results are shown in Table 7. Samples were prepared with or without 200 mM trehalose. They were frozen and then dried by SPEEDVAC without added heat, SPEEDVAC w/medium heat, or in a lyophilizer (freeze-drying). Freeze-drying with trehalose gave the best results. But all samples gave good sequencing results after drying in the absence of glycerol. Note also that because of trehalose in the buffer exchanged polymerase, the "water" sample in Table 7 had approximately 1 mM trehalose.

TABLE 7

| | 8 µl Formulation w/o primer | | | | | |
|---|---|---|---|---|---|---|
| | SPEEDVAC | | SPEEDVAC w/medium heat | | Freeze-dry | |
| | Total Signal | Phred20 | Total Signal | Phred20 | Total Signal | Phred20 |
| water | 1392 | 637 | 1767 | 666 | 1517 | 678 |
| trehalose | 1346 | 660 | 1115 | 661 | 1705 | 684 |

The elimination of glycerol gave unexpectedly superior results. The samples dried after dialyzing away glycerol had better signal strength and sequencing quality, as measured by total signal and Phred20 scores, than samples containing glycerol that were dried under comparable conditions.

Example 4

Stability of the Dried Sequencing Mixes to Storage after Freeze-drying

In this example, 5-µl sequencing reaction mixes using BIGDYE TERMINATOR v3.0 (Applied Biosystems, Foster City, Calif.) were prepared without glycerol as described in Example 3. The sequencing mix samples contained 200 mM trehalose and 0.2 mg/ml bovine serum albumin. Samples were dispensed into a 96 well reaction plate, and dried down by freeze-drying in a lyophilizer. The samples were dried with or without primer. The samples did not contain TMANO. Sequencing reactions were run before drying, immediately after drying, or following storage for up to 8 weeks at room temperature, 37° C., or 60° C. The signal strength and Phred20 score of the sequencing reactions were quantified, and the results are shown in Tables 8 and 9.

TABLE 8

BIGDYE TERMINATOR v3.0 Stability (Signal Strength)

| | before drying | after drying | 1 wk | 2 wk | 3 wk | 4 wk | 8 wk |
|---|---|---|---|---|---|---|---|
| RT w primer | 1316 | 1054 | 631 | 670 | 819 | 672 | 927 |
| RT w/o primer | 1312 | 1010 | 771 | 670 | 676 | 839 | 961 |
| 37 w primer | | | 340 | 502 | 747 | 760 | 865 |
| 37 w/o primer | | | 696 | 720 | 670 | 767 | 820 |
| 60 w primer | | | 776 | 747 | 716 | 755 | 843 |
| 60 w/o primer | | | 766 | 794 | 707 | 822 | 1009 |

TABLE 9

BIGDYE TERMINATOR v3.0 Stability (Phred Q20 Bases)

| | before drying | after drying | 1 wk | 2 wk | 3 wk | 4 wk | 8 wk |
|---|---|---|---|---|---|---|---|
| RT w primer | 643 | 640 | 656 | 653 | 684 | 648 | 674 |
| RT w/o primer | 636 | 661 | 677 | 653 | 672 | 670 | 661 |
| 37 w primer | | | 642 | 658 | 683 | 668 | 648 |
| 37 w/o primer | | | 665 | 658 | 673 | 676 | 662 |
| 60 w primer | | | 676 | 663 | 669 | 674 | 677 |
| 60 w/o primer | | | 659 | 662 | 657 | 681 | 674 |

The samples were unexpectedly stable to storage. The samples showed some decline of signal strength due to the drying, and some further decline in the first week of storage at all temperatures. But thereafter they showed stable signal quantity at approximately two-thirds of levels of the undried control even after 8 weeks storage at 60° C. Sequencing quality was also stable even after 8 weeks storage at 60° C., and moreover showed no initial decline due to drying.

REFERENCES CITED

Uritani, M., et al., *J. Biochem.* 117:774-779 (1995).
Colaco, C., et al., *Bio/Technology* 10:1007-1011 (1992).
Earley, J. J., et al., *DNA Sequence—J. DNA Sequencing and Mapping* 4:79-85 (1993).
Ortlepp, S. A., et al., *BioTechniques* 7:1110-1115 (1989).
Lee, L. G., et al., U.S. Pat. No. 6,335,440 (2002).
Lee, L. G., et al., U.S. Pat. No. 5,945,526 (1999).
Lee, L. G., et al., U.S. Pat. No. 5,863,727 (1999).
Lee, L. G., et al., U.S. Pat. No. 5,800,996 (1998).
Bergot, B. J., et al., U.S. Pat. No. 5,366,860 (1994).
Sanger, F., et al., *Proc. Natl. Acad. Sci. USA* 74:5463-5467 (1977).
Slatko, B. E., et al., in Ausubel, F. M., et al. (eds.) *Current Protocols in Molecular Biology* (New York, John Wiley & Sons), pp. 7.4.1-7.4.27 (1991).

All references referred to herein are hereby incorporated by reference. The invention has been described with reference to various specific embodiments and techniques. However, it should be understood that many variations and modifications may be made while remaining within the spirit and scope of the invention.

We claim:

1. A dry composition comprising a mononucleotide linked to a fluorescent dye, wherein the composition comprises a thermostable nucleic acid polymerase, wherein the thermostable nucleic acid polymerase is Taq DNA polymerase, wherein the dry composition is substantially free of glycerol, and wherein the ratio of glycerol to Taq DNA polymerase is less than 1 ug of glycerol per unit of Taq DNA polymerase.

2. The composition according to claim 1 further comprising a cryoprotectant.

3. The composition according to claim 2 wherein the cryoprotectant is trehalose.

4. The composition according to claim 2 wherein the cryoprotectant is sucrose.

5. A method of making the composition of claim 1 comprising the step of drying a solution comprising the mononucleotide linked to the fluorescent dye, the Taq DNA polymerase, and a cryoprotectant.

6. The method of claim 5 wherein the cryoprotectant is trehalose.

7. The method of claim 5 wherein the cryoprotectant is sucrose.

8. The method of claim 5 wherein the temperature of the solution during at least a portion of the drying step is less than 0° C.

9. The method of claim 5 wherein the dye is an energy transfer dye comprising a donor connected to an acceptor by a linker.

10. The method of claim 9 wherein the linker comprises an alkene, diene, alkyne, unsaturated five-membered ring, unsaturated six-membered ring, or a fused ring system.

11. The method of claim 10 wherein the dye has the structure

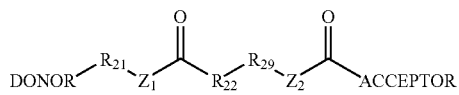

where $R_{21}$ is a $C_{1-5}$ alkyl; $Z_1$ is NH, sulfur, or oxygen; $R_{22}$ is an alkene, diene, alkyne, unsaturated five-membered ring, unsaturated six-membered ring, or a fused ring system; $R_{29}$ is $C_1$-$C_5$ alkyl; and $Z_2$ is NH, sulfur, or oxygen.

12. The method of claim 9 wherein the donor is a fluorescein, rhodamine, or asymmetric benzoxanthene dye.

13. The method of claim 12 wherein the donor is a carboxyfluorescein; 4,7-dichlorofluorescein; asymmetric benzoxanthene; rhodamine; 4,7-dichiororhodamine; carboxyrhodamine; carboxy R110; carboxy R6G; or carboxy-X-rhodamine dye; or is Cy5.

14. The method of claim 9 wherein the acceptor is a xanthene, cyanine, phthalocyanine, or squaraine dye.

15. The method of claim 14 wherein the acceptor is a 4,7-dichlorofluorescein; asymmetric benzoxanthene; rhodamine; 4,7-dichiororhodamine; carboxyrhodamine; carboxy R110; carboxy R6G; or carboxy-X-rhodamine dye; or is Cy5.

* * * * *